United States Patent
DeStefano et al.

(10) Patent No.: US 6,282,442 B1
(45) Date of Patent: Aug. 28, 2001

(54) MULTI-FIT SUCTION IRRIGATION HAND PIECE

(75) Inventors: Mark A. DeStefano, Collegeville; Stewart I. Jaffe, Downington, both of PA (US)

(73) Assignee: Surgical Laser Technologies, Inc., Montgomeryville, PA (US)

( * ) Notice: Subject to any disclaimer, the term of this patent is extended or adjusted under 35 U.S.C. 154(b) by 0 days.

(21) Appl. No.: 09/392,697

(22) Filed: Sep. 9, 1999

Related U.S. Application Data

(60) Provisional application No. 60/099,969, filed on Sep. 11, 1998.

(51) Int. Cl.[7] ............................... A61N 1/30; A61N 1/00; A61B 1/00; A61B 1/12; A61B 18/18
(52) U.S. Cl. ............................. 604/21; 604/35; 606/49; 600/121; 600/156
(58) Field of Search .................................. 604/22, 27, 35, 604/93.01, 164.01, 165.02, 523, 533, 539, 21; 600/101, 104, 121, 125, 130, 136, 137, 156; 606/32, 27, 49; 607/115

(56) References Cited

U.S. PATENT DOCUMENTS

| | | | |
|---|---|---|---|
| 4,149,315 | 4/1979 | Page, Jr. et al. | 32/22 |
| 4,579,230 | 4/1986 | Reid, Jr. | 21/13 |
| 4,744,360 | 5/1988 | Bath | 128/303.1 |
| 4,776,840 | 10/1988 | Freitas et al. | 604/33 |
| 4,904,238 | 2/1990 | Williams | 604/43 |
| 5,170,774 | 12/1992 | Heckele | 128/4 |
| 5,195,958 | 3/1993 | Phillips | 604/33 |
| 5,197,963 | 3/1993 | Parins | 606/46 |
| 5,289,555 | 2/1994 | Sanso | 385/92 |
| 5,310,406 | 5/1994 | Sharpe et al. | 604/35 |
| 5,312,332 | 5/1994 | Bales et al. | 604/49 |
| 5,322,503 | 6/1994 | Desai | 604/21 |
| 5,333,603 | 8/1994 | Schuman | 128/7 |
| 5,348,555 | 9/1994 | Zinnanti | 606/49 |
| 5,551,448 | 9/1996 | Matula et al. | 128/897 |
| 5,554,112 | 9/1996 | Walbrink et al. | 604/27 |
| 5,607,391 | 3/1997 | Klinger et al. | 604/33 |
| 5,611,813 | 3/1997 | Lichtman | 606/205 |
| 5,620,459 | 4/1997 | Lichtman | 606/205 |
| 5,662,647 | 9/1997 | Crow et al. | 606/41 |

OTHER PUBLICATIONS

Leaflet for Richard Wolf Video HydraScopic System.
Leaflet for Karl Storz Suction and Irrigation Endoscope.

*Primary Examiner*—Richard K. Seidel
*Assistant Examiner*—Michael Hayes
(74) *Attorney, Agent, or Firm*—Drinker Biddle & Reath LLP

(57) ABSTRACT

A disposable hand piece providing irrigation and aspiration capability to a surgical field can adaptably hold within itself endoscopes of different manufacturers. Running through the hand piece is a bore; attached at the distal end of the hand piece is a reusable sheath. The tubular shaft of an endoscope is inserted into the bore of the hand piece and the reusable sheath. A first collet at the proximal side of the hand piece securely holds the endoscope by adjusting to the outer diameter of the tubular shaft of the endoscope. A second collet at the distal side of the hand piece holds the reusable sheath in a selected linear extension. The collets, however, permit the tubular shaft and the reusable sheath to be rotated in place and thus adjust the view of the surgical field. An annular space is maintained between the tubular shaft and the reusable sheath so as to provide a channel for irrigation and aspiration. Further aspiration capability is provided by a separate suction device. A method of attaching an endoscope and sheath to the hand piece and using the apparatus is also disclosed.

20 Claims, 9 Drawing Sheets

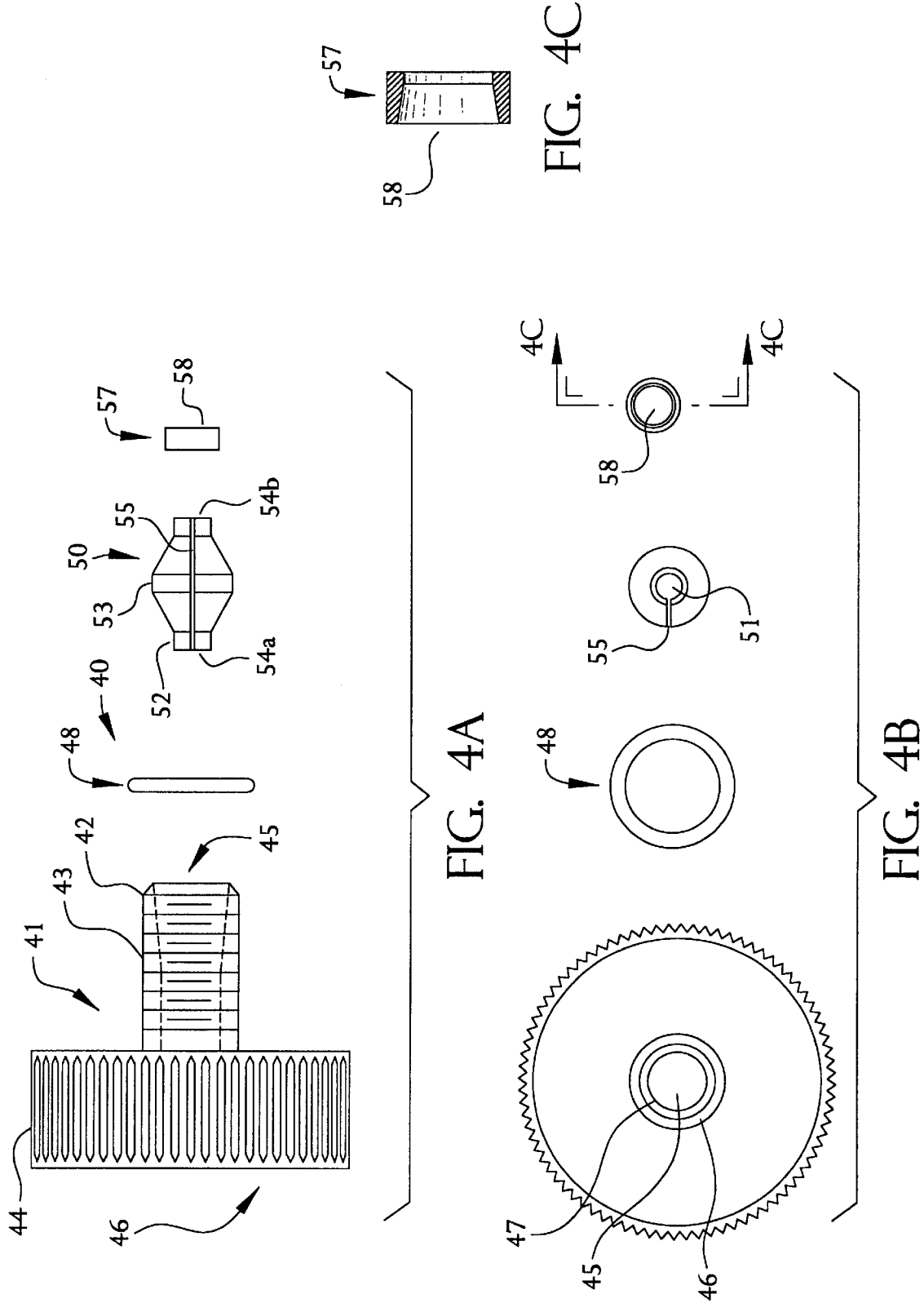

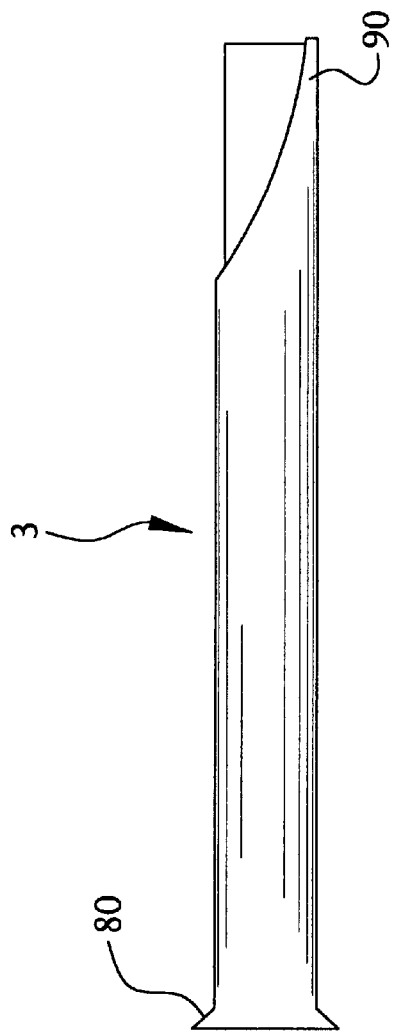
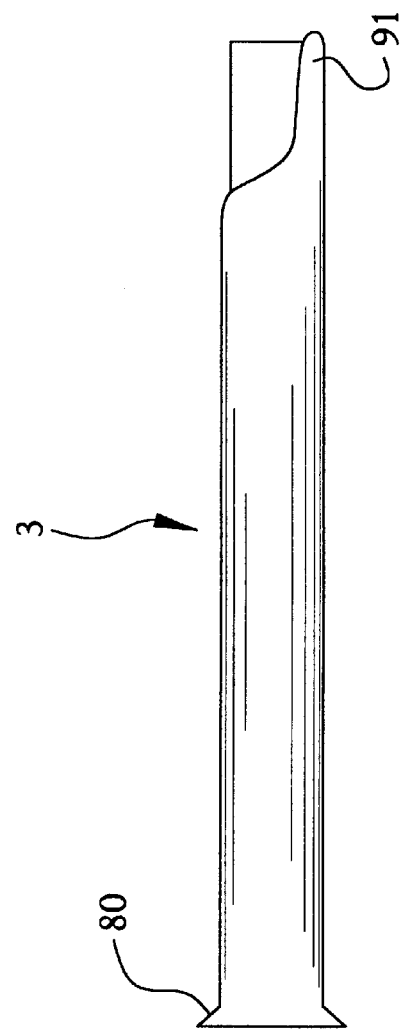

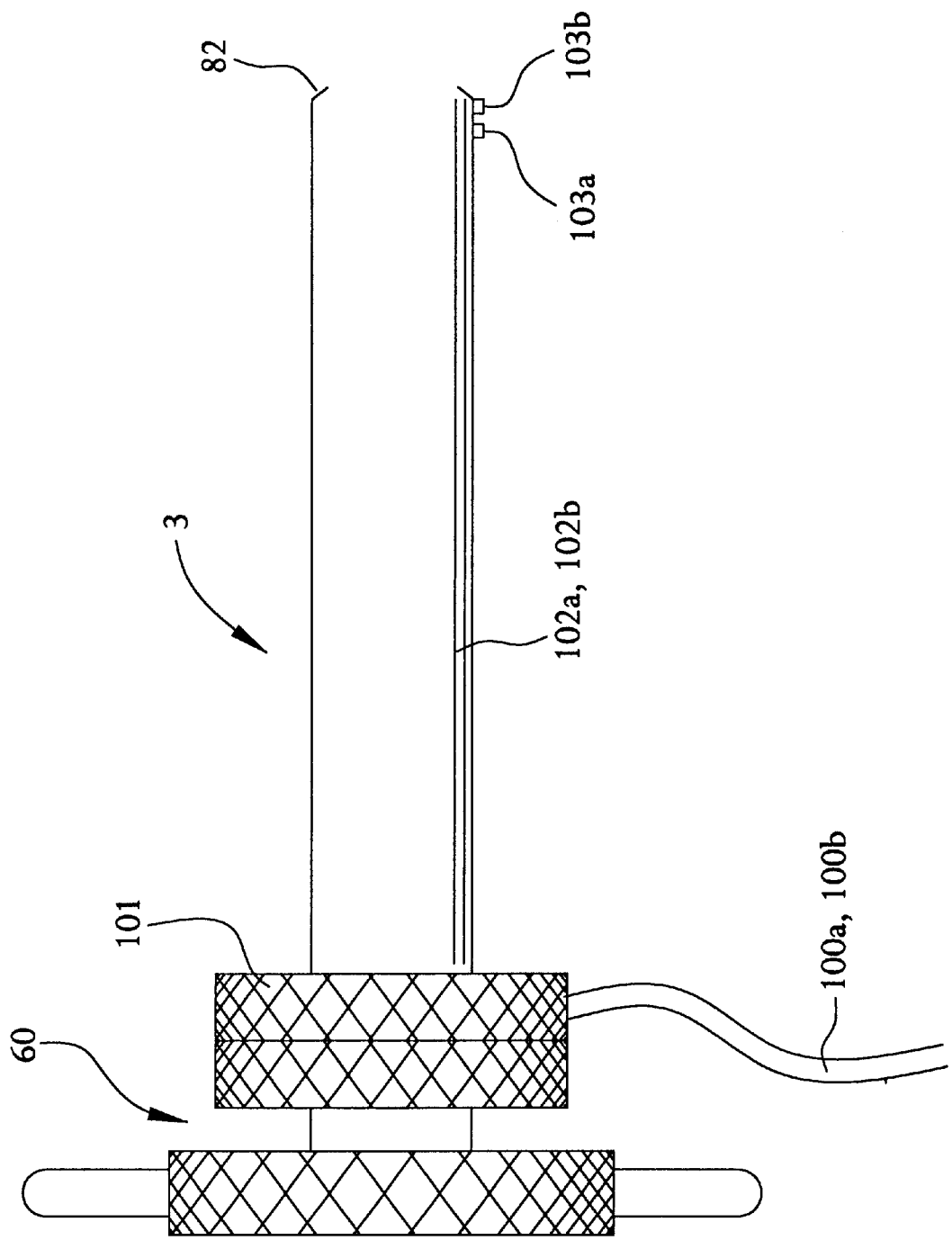

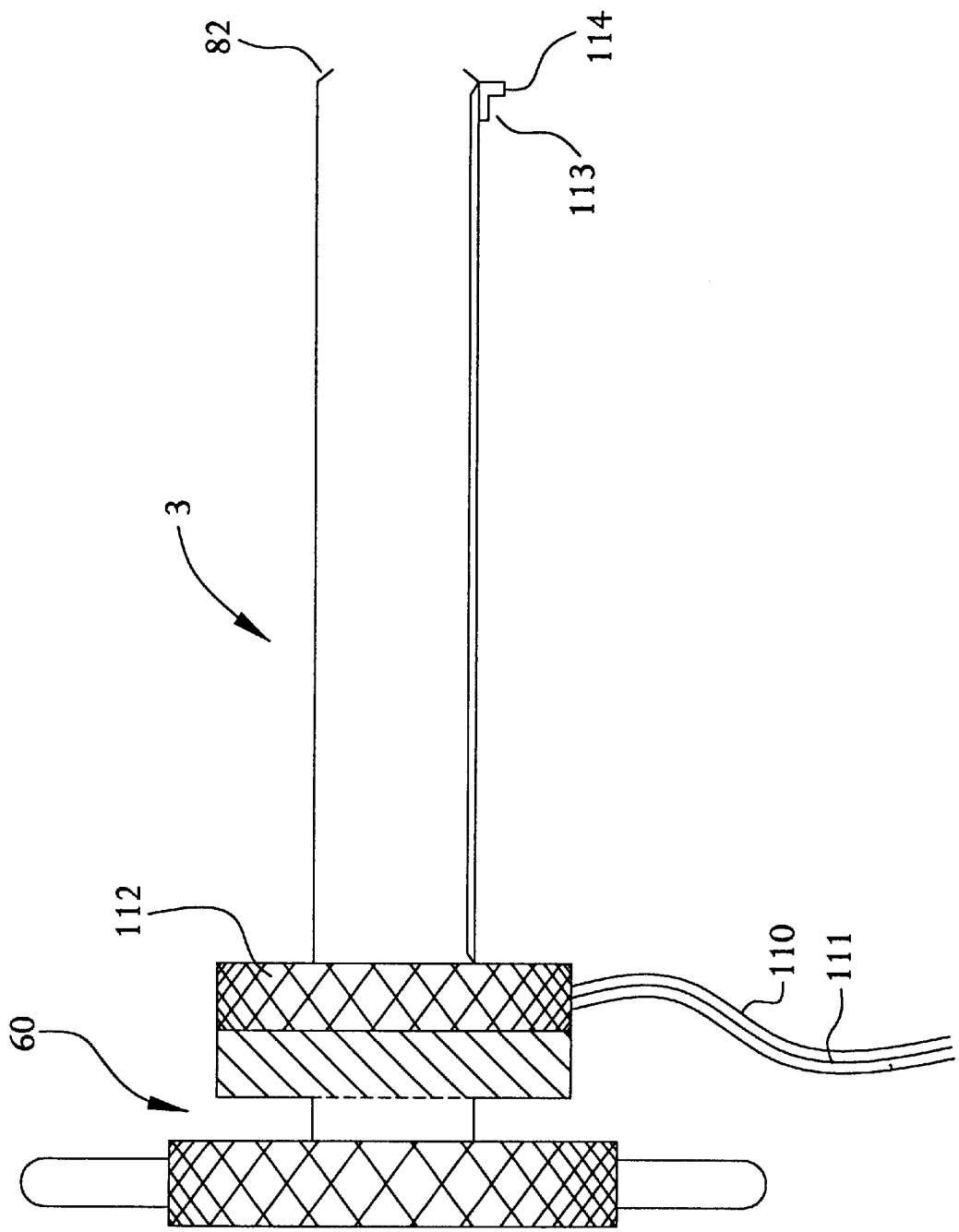

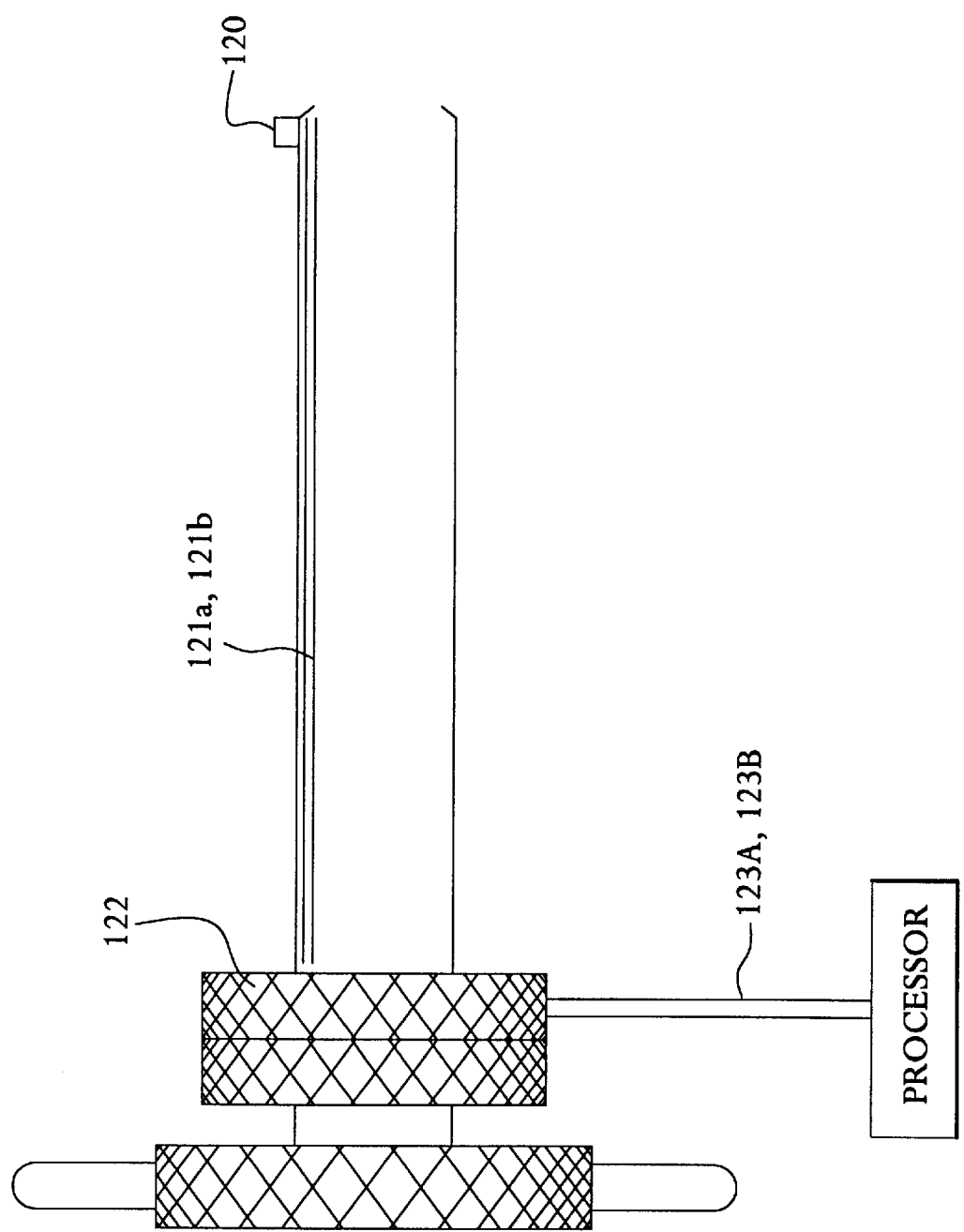

MULTI-FIT SUCTION IRRIGATION HAND PIECE

This application claims benefit of Provisional Appln. 60/099,969 filed Sep. 11, 1998.

FIELD OF THE INVENTION

The present invention relates to a surgical hand piece that can be adaptably used in conjunction with different vendors' endoscopes. The hand piece provides irrigation to a surgical field and aspiration from the surgical field. Also described are enhancements to the invention, comprising mechanical, laser, electrosurgical, drug delivery and real-time imaging capabilities.

BACKGROUND OF THE INVENTION

Surgeons have traditionally operated on the internal organs and other internal structures of the human body by laying the body open to provide access for the operation. In recent decades, however, some surgeons have employed devices and techniques by which such access can be provided without laying open the body. Such means have been described variously. Two such descriptions are "minimally invasive surgery" and "endoscopy".

The first description, "minimally invasive surgery", alludes to the fact that the access to the site can be gained by small incisions made by trocars and cannulas.

The second description, "endoscopy", alludes to the fact that a surgeon uses an endoscope to view the surgical field and tissue effects produced by instrumentation, as for example devices which cut or coagulate tissue. In certain contexts, "endoscopy" is used to refer to non-invasive surgery using the body's own lumens and cavities for access, whereas in other contexts the term is also used to refer to invasive surgery where small incisions are made in the body by trocars and such access is further secured by cannulas. Here, the term "endoscopy" is meant to include both non-invasive and invasive approaches. The term "endoscope" is meant to incorporate a host of viewing devices that provide visibility to a surgeon in minimally invasive surgery. Among such endoscopes, for example, are arthroscopes, bronchoscopes, cystoscopes, hysteroscopes, laparoscopes, laryngoscopes, nephrescopes, resectoscopes and sinuscopes.

Ancillary to many surgical operations are irrigation and aspiration of the surgical field. Irrigant can broadly serve to wash and cleanse the tissue and to clear the field of view of such interference as blood or tissue debris. Irrigant can also, depending upon its temperature, pressure, volume and composition, serve a narrower specific therapeutic purpose, as for example it may selectively dissect tissue, or it may effect vasoconstriction of certain tissues.

Aspiration may serve a broad role in evacuating irrigant, blood and tissue debris from the surgical field. Aspiration may also serve a narrower role in keeping the optics of an endoscope free from interference.

Necessarily, it is beneficial in endoscopy to maximize the surgical capabilities that can enter a corporal orifice or slip down a single cannula and thus minimize the time and effort in removing and inserting surgical instruments into and from such orifices or cannulas. It becomes desirable for a single orifice or cannula to accommodate multiple surgical instrumentalities simultaneously. Thus, a single endoscopic device that can both cut tissue mechanically and provide laser or electrosurgical coagulation can save significant time in the operating room and thus reduce the time during which a patient is at surgical risk. In similar fashion, an endoscopic device that provides visibility of the surgical field and also provides irrigation and aspiration, in both their broad and narrower roles, can likewise save time and reduce risk. Properly designed, such an endoscopic device can also provide electrosurgical or laser coagulating capability.

Among the leading vendors of endoscopes are such manufacturers as Karl Storz of Tuttlingen, Germany; Richard Wolf of Knittlingen, Germany; Circon ACMI of Santa Barbara, California; and Olympus Optical of Tokyo, Japan. Naturally, the endoscopes of the various manufacturers will have differing structural and operating characteristics, and naturally some surgeons will have decided preferences for one endoscope over another. A single hospital may have a sinuscope by Karl Storz in one operating room, and a sinuscope by Richard Wolf in a different operating room.

However, the leading endoscopes have one primary feature in common: they all have a tubular shafts that can enter directly a corporal orifice or slip down a cannula. Many endoscopes addressing the same surgical function also have tubular shafts of similar lengths. This is, for example, the case for many sinuscopes, which have tubular shafts of approximately 4 mm in outer diameter and 170 mm in length. It is desirable, therefore, to provide a device by which ancillary irrigation and aspiration can supplement any of the leading endoscopes. A hospital would thereby not be obliged to carry multiple irrigation/aspiration devices for various endoscopes.

Significant concern exists nowadays over the spread of disease within nosocomial institutions. The HIV virus and autoimmune deficiency syndrome (AIDS) have heightened this concern. Also, it can be problematic to clean and sterilize an irrigation/aspiration hand piece after use and possible exposure to disease, having as it does intricate valves and passageways blocked from ready view. A valve system, moreover, is susceptible to wear and deterioration in such components as O-rings and other seals. It is desirable that a device providing ancillary irrigation and aspiration should be inexpensively produced and therefore economical to be used in a single procedure and then disposed of in accordance with proper disposal procedures. Such a product, called a disposable, allays concerns that resterilization may be effective against infection from certain communicable diseases.

U.S. Pat. No. 4,149,315 to Page, Jr. et al. describes a suction/irrigation device for dental surgery. The hand grip of the device is shaped like a pistol. An elongated tube includes a pair of concentric tubes. The inner tube supplies irrigant; the outer tube provides suction. Two trumpet valves regulate the irrigant and aspirant. To similar effect is U.S. Pat. No. 4,776,840 to Freitas et al., where the described device entails an internal pump to supply the irrigant and also a separate flexible tube for additional suction of the surgical site.

U.S. Pat. No. 4,744,360 to Bath discloses a suction/irrigation device for use in ophthalmic surgery. Surrounding an optical fiber for laser surgery are an irrigation sleeve and a separate aspiration sleeve which provide irrigation and suction capability, respectively.

U.S. Pat. No. 5,170,774 to Heckele discloses an endoscope with lateral viewing capability and with separate channels for gentle irrigation, high pressure irrigation and aspiration. The irrigant exits its channel at such an angle that it will impact the tissue being treated within the field of view of the endoscope. A nozzle on the end of the high-pressure channel may be changed to vary the pressure. Thus a surgeon may immediately observe whether the irrigant is having the effect that is desired.

U.S. Pat. No. 5,195,958 to Phillips discloses a device for minimally invasive surgery which provides irrigation, suction and evacuation of the surgical site. Various attachments may be attached to and detached from a hand piece.

U.S. Pat. No. 5,197,963 to Parins discloses a device which provides irrigation, aspiration and electrosurgery. A sheath encloses a cylindrical rod. Within the rod are at least one electrosurgical electrode and a lumen for irrigation and aspiration. The sheath protects the electrode from breakage during insertion or withdrawal from the surgical site. The sheath may be retracted, and thus expose the electrode for use. If the sheath is extended beyond the electrode, the sheath effectively provides an extended path for the irrigant or aspirant.

Various patents describe suction/irrigation devices which can receive, through a special port, other instrumentation to be used at the surgical site. U.S. Pat. No. 5,310,406 to Sharpe et al. discloses a large diameter tube which has a port concentric with the tube through which a grasping tool may be inserted. U.S. Pat. No. 5,312,332 to Bales et al. describes a valve through which a tool for minimally invasive surgery may be inserted. U.S. Pat. No. 5,322,503 to Desai illustrates a suction/irrigation device which includes a port for receiving endoscopic instrumentation. Also illustrated are an electrosurgical capability and a detachable probe that can be used with a variety of working tips.

In U.S. Pat. No. 5,333,603 to Schuman there is described an endoscope with a palm rest formed on a stem of an endoscope. Valves reside formed in the stem and have controls for the flow of irrigation and suction.

U.S. Pat. No. 5,348,555 to Zinnanti describes a device which supplies suction, irrigation and cautery to a surgical site. The valve body and sheath of the device are transparent so that a surgeon may observe whether a tissue sample has been procured. The device has connection ports on both ends, so that the device can be used by right- and left-handed people. Since the sheath is plastic, it resists capacitive coupling from an electrosurgical needle that may be used in the sheath.

U.S. Pat. No. 5,554,112 to Walbrink et al. describes aminimally invasive irrigator/aspirator device with a probe. A handle of the device can be rotated about a rotational axis separate and independent from the longitudinal axis of the probe. The probe may likewise be rotated about its own longitudinal axis, in a manner separate and independent of rotation of the handle. Also disclosed are an electrode assembly and a mechanism to lock the valves and thus regulate the aspiration and irrigation.

U.S. Pat. No. 5,551,448 to Matula et al. describes an endoscopic device providing suction and irrigation. The described device allows for at least one of its trumpet valves to be rotated at least 180 degrees, thereby allowing a surgeon to adjust the position in which the device is held. The device also has electrosurgical capability.

Related to Matula et al. is U.S. Pat. No. 5,607,391 to Klinger et al., which discloses an endoscopic instrument for aspiration and irrigation. A single-lumen cannula delivers irrigant and removes aspirant. A valve mechanism is disclosed for increasing the pressure of the irrigant so that it can perform hydrodissection. The cannula can be given electrosurgical capability. Also disclosed is a detachable cannula assembly which provides different working tools to the end of the cannula. Such tools include spatulas, cutters, hooks and the like. A sliding outer sleeve on the cannula can be used to protect or expose the working tools.

An electrode assembly that can be detachably combined with an aspiration/irrigation cannula is disclosed in U.S. Pat. No. 5,662,647 to Crow et al.

The electrode assembly slides within the cannula to reach the surgical site. The patent also discloses an electrosurgical method employing the apparatus described in the patent.

Karl Storz markets a family of endoscopes having a straight, rigid tubular shaft. In one member of the family, the field of view is straight ahead of the lens at the distal end; in another member, the field of view is canted 30 degrees from straight ahead. The proximal end of the tubular shaft has a unique contour that couples only to the proximal end of a hand piece. The hand piece is relatively heavy and does not allow one hand to control suction, irrigation and placement of the scope.

In similar fashion, Richard Wolf markets a family of endoscopes having a straight, rigid tubular shaft. In scopes within the family that have fields of view straight ahead, some subtend a field of view of 70 degrees, others subtend a field of view of 120 degrees. Others have a field of view canted 25 degrees from straight ahead. Like its Karl Storz counterpart, the Wolf endoscope uniquely couples to a Wolf hand piece. The hand piece is relatively heavy and bulky and does not permit a surgeon to control irrigation, suction and visualization in one hand.

On balance, none of the devices known in the prior art describes how a single suction/irrigation hand piece may be devised such that it may be usable within the same surgical specialty with the endoscopes of various manufacturers.

Furthermore, none of the devices known in the prior art enables a surgeon to use a single hand to control suction, irrigation and visualization, leaving the other hand free to wield different instruments.

None of the devices known in the prior art teaches an adjustable linear extension of the sheath capable of fitting over the tubular shaft of different endoscopes, or a rotatable tubular shaft or sheath that allows the surgeon to adjust the position of the hand piece for greater comfort and a better view.

The prior art does not disclose a device that can provide irrigation for keeping the surgical field and the distal end of the scope clear of blood and debris while at the same time providing suction for continuous evacuation of the surgical field and simultaneously providing selective aspiration of the area adjacent to the distal end of an endoscope.

It is therefore an object of this invention to provide a hand piece which can alternately supply irrigation and aspiration to a surgical field down a single channel of a sheath attached to the hand piece, and which can be readily adapted to hold an endoscope. The invention will thus put control of suction, irrigation and visualization of the surgical field into a single hand of the surgeon, and thus free the other hand for other use.

Another object of this invention is to provide a means by which a single hand piece can be adjusted so as to adapt to and firmly hold the endoscopes of a variety of manufacturers, and do so without leaks.

Another object of this invention is that such a hand piece can keep the surgical field clear of blood and debris in a convenient manner as well as keep the face of the endoscope clean of visual interference.

It is yet another object of this invention that the same source of suction that provides aspiration through the sheath can provide continuous evacuation of irrigant, blood and debris.

A further object of the invention is to adjoin selected capabilities of mechanical instruments as well as coagulating capability to the hand piece and sheath.

Further objects of the invention are to enhance the view of the surgical field by means of real-time imaging and to render the invention compatible with magnetic resonance imaging.

It is a further object of this invention that such a hand piece should be lightweight and convenient to use. The hand piece should be inexpensively manufactured and therefore rendered a disposable item in the operating room, whereas the sheath should be able to be resterilized and reused.

SUMMARY OF THE INVENTION

The invention comprises a hand piece which provides irrigation and aspiration to a surgical field and which adaptably holds within itself endoscopes of different manufacturers.

Running through the hand piece is an axial bore. A sheath is removably attached to the bore at the distal end of the hand piece. A bayonet pin arrangement is one means of such attachment, where the bayonet pins are set on a hub encircling the sheath and the grooves for the pins are set into the distal bore of the hand piece.

The tubular shaft of an endoscope is inserted into the proximal end of the bore, through the bore and into the sheath. An annular space exists between the tubular shaft and the sheath. The annular space communicates with the bore of the hand piece, which in turn communicates with trumpet valves, described below.

As different endoscopes may have tubular shafts of differing lengths, the length to which the sheath extends from the hand piece may be correspondingly adjusted so the distal end of the sheath and the distal end of the tubular shaft may terminate flush with each other. This adjustment is enabled by the fact that a portion of the length of the sheath may reside within the bore in the hand piece.

The hand piece has two trumpet valves, one to regulate the irrigation, and the other to regulate the aspiration. Flexible tubing connects each valve to a source of irrigation or suction, respectively. The irrigant enters an inlet valve through a connection port and flows into the axial bore of the hand piece and thence into the annular space existing between the tubular shaft of the endoscope and the sheath. The irrigant exits at the distal end of the sheath and debouches into the surgical field. Aspirant is withdrawn at the distal end of the sheath, flows back through the annular space and exits the hand piece through the aspiration port to a reservoir associated with the suction source. The inlet ports may receive the flexible tubing at right angles to the axial bore of the hand piece; alternately, the ports may receive the tubing at an acute angle to the axial bore of the hand piece, thus a different orientation to the user. In yet a different embodiment, the valves can be made to swivel, and thus the orientation of the inlet ports may be adjusted.

The temperature of the irrigant can be controlled, to be either hot, warm or cold, for a desired thermal effect. Irrigation can be pressurized for more forceful lavage or hydrodissection; liberal irrigation can gently part soft tissue that lies over other tissue that is to be treated. Irrigation can also be used to point the way to tissue otherwise hard to discern. For example, a trail of bubbles from the irrigant may emerge from the sphenoid ostium and thus point the way to the sphenoid sinus.

Additional suction of the surgical site may be obtained by means of a suction nozzle separate from the hand piece and sheath. Tubing leading from the common source of suction branches into two tubes. The one tube leads to the aspiration port on the hand piece. The other tube leads to a separate nozzle which may be placed at or near the surgical site. Such nozzles are commonly used, for example, in dental procedures. The path for aspiration within the sheath lies in the annular space between the sheath and the tubular shaft of the endoscope and is thus constrained in the volume of aspirant that may be removed and may clog due to tissue particles. The catheter path for the suction nozzle is not so constrained. Therefore the path of the suction nozzle may be used for continuous evacuation of the surgical site, including tissue debris, whereas the aspiration path within the sheath and hand piece may be reserved for clearing the field of view of blood and smaller volumes of irrigant.

A first collet at the proximal end of the hand piece holds the tubular shaft of an endoscope within the bore in the hand piece. The first collet prevents radial and axial movement of the endoscope. The first collet includes a compression fitting positioned between a seat or bushing seated within the hand piece bore and a locking nut, which is threadedly attached to the hand piece. The compression fitting includes a longitudinal slot that enables the interior diameter of the fitting to decrease as the locking nut moves into the hand piece bore. As such, the fitting adapts to the diameter of the tubular shaft of the endoscope and secures a snug grip thereon. Other means may be used as well in order to adapt the hand piece to fit an endoscope.

A second collet, at the distal end of the hand piece, holds the sheath at a selected linear extension. A compression fitting is squeezed between the distal side of the hub bearing the bayonet pins and a locking nut, which threads into the distal side of the hub. Other means may be used as well in order to adapt the length of the sheath to conform to the length of an endoscope.

Nevertheless, the first collet will permit, with a reasonable torque, the endoscope to be slightly rotated within the bore of the hand piece and sheath. This is particularly useful in adapting to endoscopes having fields of view canted from a field of view in line with the axis of the tubular shaft. Likewise, the second collet will permit the sheath to be slightly rotated. Thus, as the endoscope may need to be held in varying positions to achieve the right field of view, the hand piece and sheath may also be adjusted to the new field of view.

The distal end of the sheath may be shaped so as to function like mechanical, hand-held instruments. A portion of the distal rim of the sheath may be pointed and sharpened to enable tissue cutting, like a surgical scalpel. Alternately, a portion of the distal rim may be bluntly tapered and rounded to enable blunt dissection, like a surgical spatula.

Electrosurgical capability may be imparted to the sheath. Electrical cables connect to an electrosurgical generator and lead into a hub that slips onto the sheath and abuts the sheath locking nut. Electrical conductors lead from the hub, either embedded in the sheath or overlaid upon the sheath, to the distal end of the sheath. Each conductor terminates in an exposed prominence near the distal end of the sheath, such that a bipolar electrical circuit is closed when tissue is held within and between the prominences. Alternately, the conductors terminate near the distal end of the sheath and are connected by a conductive bar having relatively greater resistance, such that the conductive bar provides ohmic heating. Whether the conductors are within or upon the sheath, means are provided to insulate the conductors from leaking from the intended electrical circuit and to hold the conductors stable.

Laser capability may be imparted to the sheath as well. An optical fiber, protected by a loose coaxial jacket or sheath, connects to a laser source and leads into a hub that slips onto the sheath and abuts the sheath locking nut. The optical fiber leads from the hub and is overlaid on and secured to the surface of the sheath. The optical fiber terminates near the distal end of the sheath. A small fiber hub fitted to the coaxial fiber jacket at the distal end of the fiber allows various laser probes to be threadedly attached to the fiber. Among such probes are ones that may be used for forward or lateral coagulation or vaporization of tissue, either in contact with the tissue being treated or not. Such probes may be cooled by a coolant that flows in an annular space between the optical fiber and the coaxial fiber jacket.

A nozzle, instead of a probe, may be mounted to the fiber hub at the distal end of the fiber, and the pressure forcing fluid through the annular space between the optical fiber and the coaxial jacket may be increased. The increase in pressure and the constricted outflow from the nozzle enable a directed flow of fluid to the tissue site. As in the case of the irrigant, it is possible to heat such fluid to achieve specific therapeutic effects. The coaxial fluid may be used to deliver drugs to the surgical site.

Enhanced visualization of the surgical site may be achieved by image-guided surgery. A sensor is placed at the distal end of the sheath, so that it can provide a view of the location of the underlying sheath and endoscope. Cables from a sensing monitor lead to a hub that slips onto the sheath and abuts the sheath locking nut. Leads connect to the cables within the hub and continue to the sensor. The leads may be protected from surgical rigors by surface securing means similar to those holding an optical fiber or electrosurgical conductors to the surface of the sheath.

The invention may be rendered compatible with magnetic resonance imaging ("MRI"), which is used to guide a surgeon in certain surgical procedures, especially in neurosurgery. In order to have minimal distortion or interference on the magnetic field, the metal components of the invention should be made of a noninterfering substance, as for example titanium.

The hand piece can be inexpensively made of plastic, and therefore rendered a disposable, to be discarded after a single surgical procedure. The sheath, on the other hand, being generally cylindrical with a smooth uniform inner bore, lends itself to ready cleaning and resterilization and therefore can be inexpensively made of a surgical grade metal and re-used.

DESCRIPTION OF THE DRAWINGS

For the purpose of illustrating the invention, there are shown in the drawings forms of the invention which are presently preferred; it being understood, however, that this invention is not limited to the precise arrangements and instrumentalities shown.

FIGS. 4A–4C show a side view and a front view of the components of the first collet and the corresponding portions of the hand piece.

FIGS. 7A–7B shows side views of a sheath shaped at the distal portions so as to provide suitable mechanical surgical action.

FIG. 8 shows a side view of a hand piece and sheath with bipolar and resistive electrosurgical capability.

FIG. 9 shows a side view of a hand piece and sheath with laser capability.

FIG. 10 shows image-guided viewing capability mounted to a sheath.

PREFERRED EMBODIMENT OF THE INVENTION

While the invention will be described in connection with preferred embodiments, it will be understood that it is not intended to limit the invention to those embodiments. On the contrary, the following description is intended to cover all alternatives, modifications, and equivalents as may be included within the spirit and scope of this invention as defined by the appended apparatus and disclosed method of use.

In the parlance of medical devices, the term "proximal" or "aft" designates an aspect of a device that is closer, or more proximate, to a user of the device than another aspect of the device. On the other hand, the term "distal" or "fore" designates an aspect of a device that is farther, or more distant, from a user than another aspect of the device.

In addition, in describing the structure of the inventive apparatus, dimensions parallel to the longitudinal axis of the apparatus are axial "lengths" along a z-axis. The other dimensions are radial "depths", measurable in an x-y plane.

Figure 1:
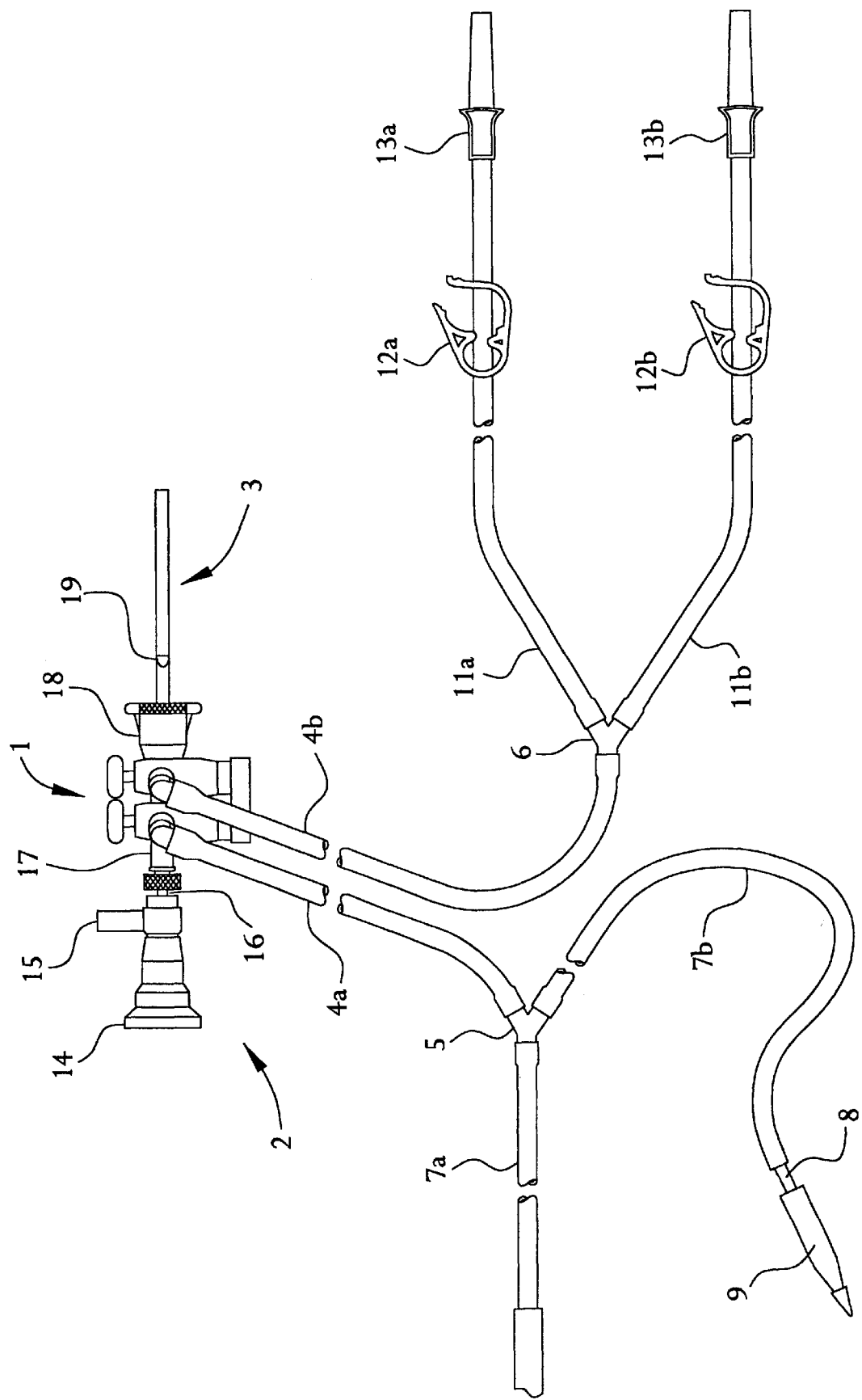
FIG. 1 shows a full side view of a surgical system contemplated by the present invention. Included in the system are a hand piece, a sheath, an endoscope, a source for irrigation and a source for aspiration, and tubing. Also shown is ancillary means drawing suction from the same source of aspiration.

Turning to FIG. 1, a preferred embodiment of the invention comprises a hand piece 1 which provides irrigation and aspiration to a surgical field and which is capable of adaptably holding endoscopes of different manufacturers. The hand piece 1 has a cylindrical, bored stem 17 at its proximal end and a flared, bored stem 18 at the distal end of the hand piece. For example, Circon ACMI of Santa Barbara, Calif. manufactures a suitable hand piece body with dual trumpet valves designed for use with surgical instruments (but not endoscopes) under the trademark "Surgiflex" which may serve as a template for the hand piece of the present invention.

An endoscope 2 is shown fitted within the hand piece I. A sheath 3 is fitted within the distal end of the hand piece 1. The endoscope 2 includes an eyepiece 14. Extending longitudinally from the eyepiece 14 is a tubular shaft 16. The tubular shaft 16 runs through the hand piece 1 and through the sheath 3, terminating flush or near flush with the distal end of the sheath 3. Fore of eyepiece 14 is light post 15, which connects to a light source which is used to illuminate the surgical field through many small optical fibers leading from the light post to the distal end of the tubular shaft 16.

Figure 2:
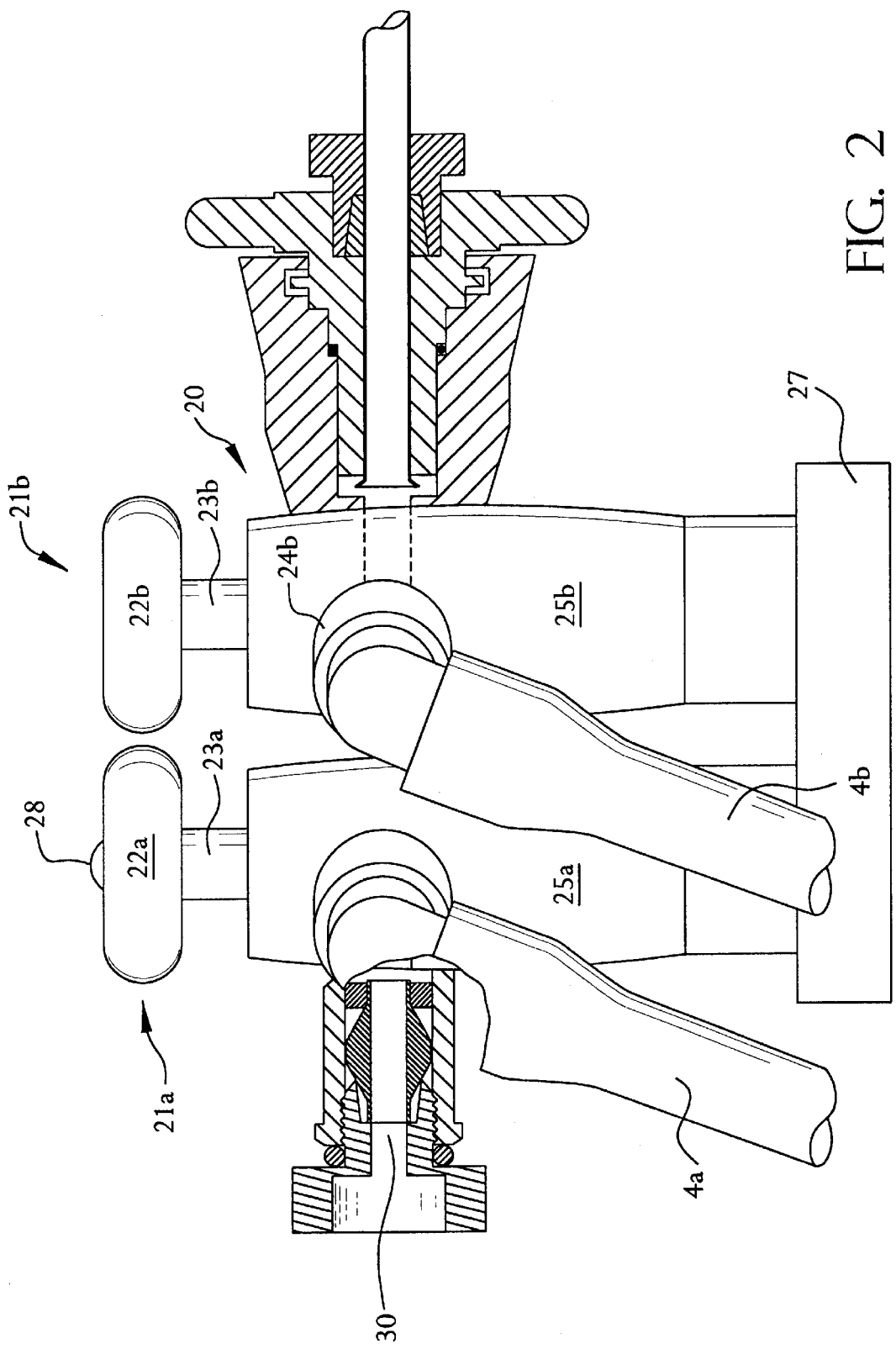
FIG. 2 shows an enlarged side view of the endoscope, hand piece and sheath, partly in section.
Figure 3:
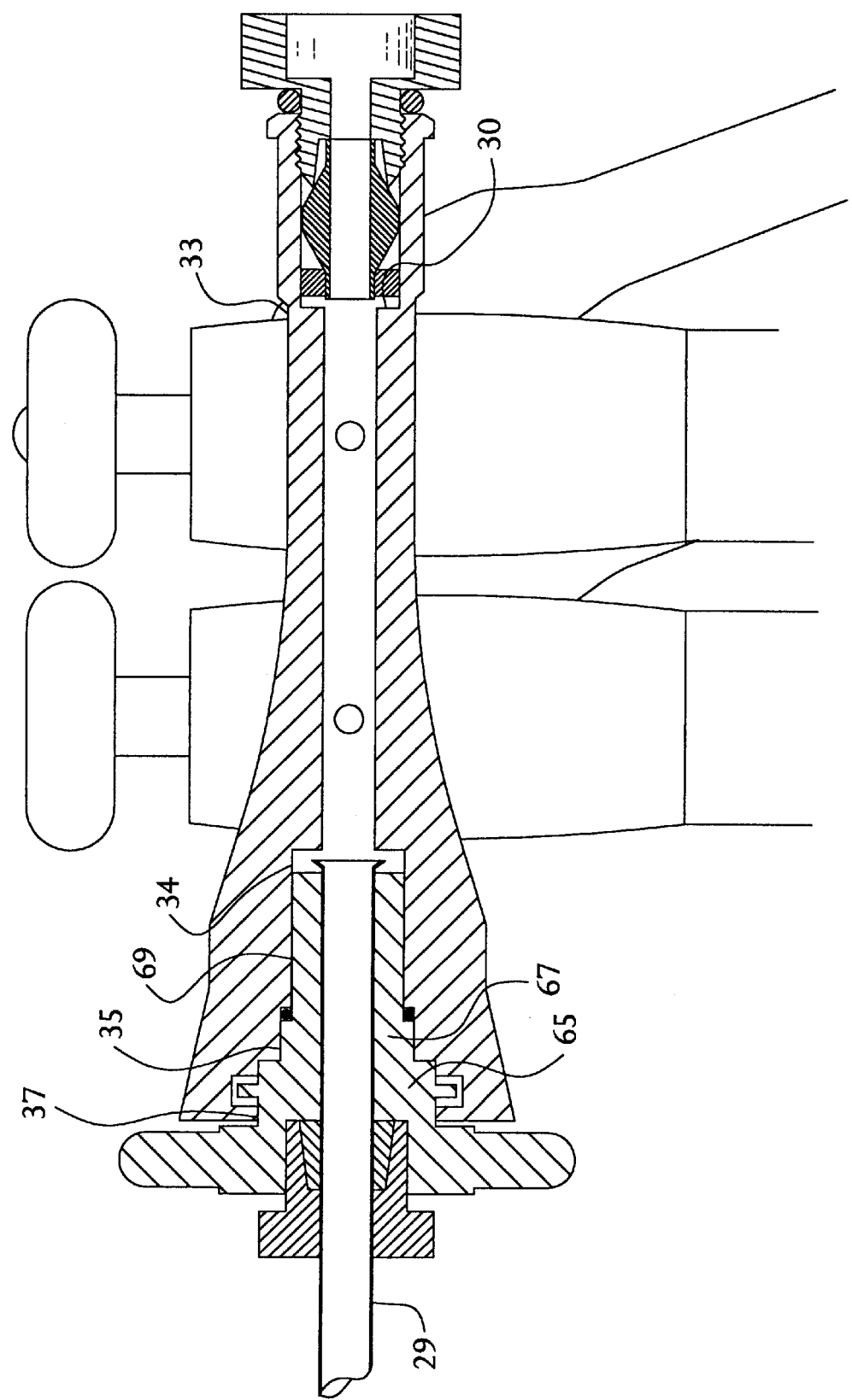
FIG. 3 shows a similar view from the other side.
Figure 5A:
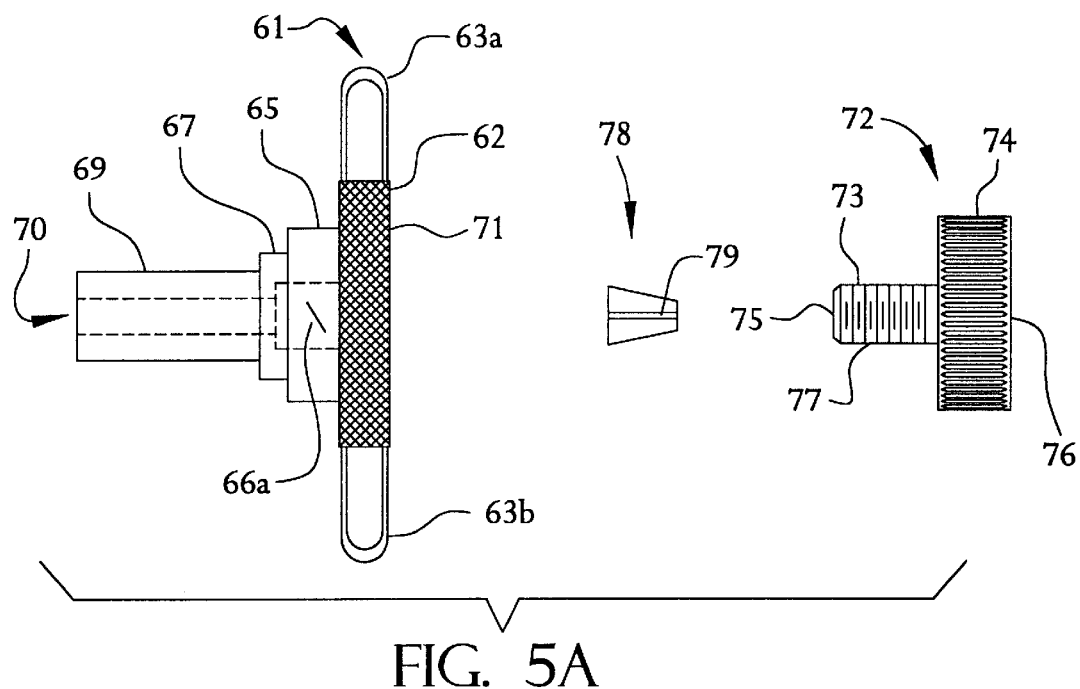
FIGS. 5A–5B shows a side view and a front view of the components of the second collet and the corresponding portions of the hand piece.
Figure 5B:
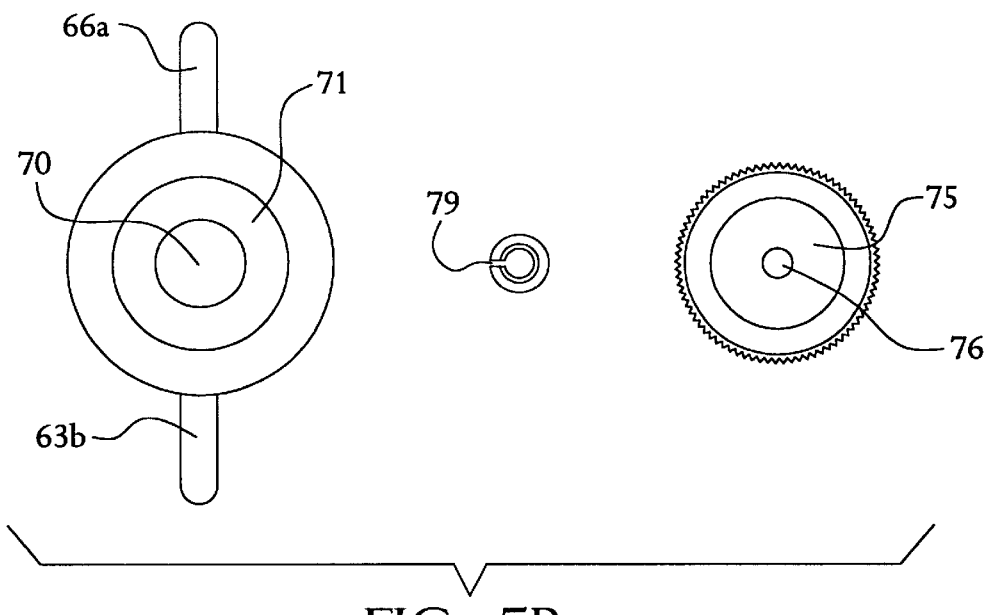
Figure 6:
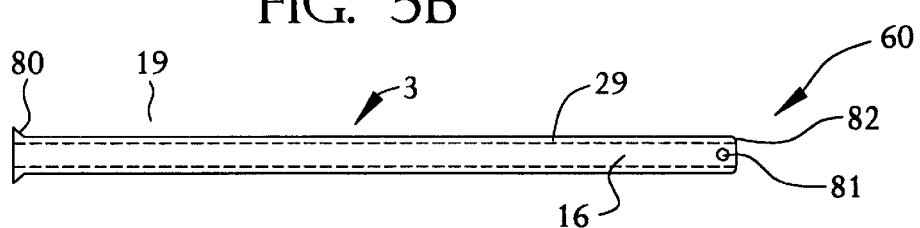
FIG. 6 shows a side view of the second collet assembled onto the sheath.

Referring to FIG. 2, the present invention includes a first collet arrangement 40 that holds the endoscope 2 within the hand piece 1. The present invention also includes second collet 60 that holds the sheath 3 within the hand piece 1. The sheath 3 is flattened slightly at region 19, causing it to adopt an oblong profile from region 19 to the distal end of the sheath.

Referring again to FIG. 1, a pair of flexible tubes 4a and 4b connect to the hand piece 1. One of the tubes 4a, provides suction. This tube 4a leads to a first Y-connector 5. The Y-connector 5 connects the suction tube 4a to a flexible tube 7a, which in turn leads to a source of suction (not shown) and associated reservoir (not shown) and a flexible tube 7b which in turn leads to a standard slip fitting 8, which connects to tube 9. Tube 9 may be malleable, or merely flexible. Tube 9 has at its distal end a suction nozzle 10. Suitable tubing is widely available.

Suction nozzle 10 can be placed at or near the surgical site to provide continuous evacuation of the surgical site of blood, irrigant and tissue debris. In contrast, the aspiration path within the hand piece can be used to clear the field of view of blood and other visual obstructions.

In sinus procedures, it is convenient to place nozzle 10 at the nasopharynx. Colorplast makes a suitable nozzle, and Sherwood Argyle makes a suitable barb connector. Suction is commonly available in wall hook-ups, or from pumps, found in an operating room. The suction can be regulated in volume and pressure. A canister is commonly used as a reservoir.

The other tube 4b receives irrigant from a second Y-connector 6. This Y-connector 6 connects the irrigation tube 4b to two tubes 11a and 11b, which in turn connect through separate spikes and covers 13a and 13b, respectively, to separate sources of irrigant (not shown). C-clamps 12a and 12b on tubes 11a and 11b may be used to restrict the flow of irrigant. If irrigant is drawn through tube 11a, then clamp 12a is loosened and clamp 12b is closed. Conversely, if the source of irrigant for tube 11a is depleted, then clamp 12a is closed and clamp 12b is loosened, thus permitting a back-up source of irrigant to be delivered through tube 11b.

The source of irrigant (not shown) may be a bag of saline set at a height (ca. 9 feet) which provides gravity feed. Alternately, if flow with greater pressure and volume is desired, a pump (not shown) or pressure cuff (not shown) may be used in conjunction with an irrigant source. Irrigant delivered at 250 mm Hg pressure suffices to flush the scope lens of interference.

For a closer view of hand piece 1, we turn to FIG. 2. Depicted in FIG. 2 are endoscope 2 with tubular shaft 16, sheath 3 and tubes 4a and 4b.

A valve assembly 20 comprises the bulk of the hand piece 1. The valve assembly 20 has two trumpet valves. A first trumpet valve 21a for regulating suction, has a finger button 22a that is connected to a valve stem 23a. When the valve stem 23a is depressed, a suction port 24a is opened and thus communicates with a bore 30 that runs through the length of hand piece 1. Seated at the bottom of the valve housing 25a for the valve stem 23a is a spring (not shown) that returns the valve to a closed position when pressure on a finger button 22a is released.

In similar fashion, a trumpet valve 21b, for regulating irrigation, has a finger button 22b that is connected to a valve stem 23b. When the valve stem 23b is depressed, an irrigation port 24b is opened and thus communicates with the bore 30. Seated at the bottom of the valve housing 25b for the valve stem 23b is a spring (not shown) that returns the valve to a closed position when pressure on a finger button 22b is released.

A plastic cap 27 slips onto the bottom of the housing for valve stems 23a and 23b. It provides a comfortable, uniform surface that may rest in the surgeon's palm.

When the irrigation trumpet valve 21b is depressed, irrigant flows through the irrigation port 24b, into an annular space between the tubular shaft 16 and the sheath 3 and debouches at the distal end of the sheath 3. When the aspiration trumpet valve 21a is depressed, fluid and debris at the distal end of the sheath 3 are withdrawn through the annular space 29 between the sheath 3 and the tubular shaft 16, through aspiration port 24a and to a reservoir (not shown) associated with the source of suction; the reservoir holds the fluid and debris. The trumpet valves 21a and 21b may be depressed simultaneously, but it is intended that they would be actuated in alternation, so that they do not reciprocally cancel their discrete effects.

It should be understood that port 24a may alternately be used for irrigation and port 24b may be used for suction. A small blister 28 may be formed on one of the finger buttons 22a or 22b in order to differentiate between which one has been selected for suction and which one for irrigation.

The inner diameter of the hand piece bore 30 is not uniform, but varies in discrete segments to accommodate different functions. Starting from stem 17 at the proximal end of the hand piece, the hand piece bore at its proximal end has a proximal 31 segment, which has an inner diameter larger than the outer diameter of the tubular shaft 16 of the endoscope 2. The proximal segment 31 is female-threaded on its inner surface. At the distal end of the threading is a small internal ridge or detent 32. The proximal segment 31 and the detent 32 are designed to interact with a first collet 40 (discussed below) which holds the endoscope 2 fixed and firm, axially and radially.

Beyond detent segment 32, the bore continues as medial segment 33, adopting an inner diameter slightly larger than the greatest outer diameter of the endoscopes which may be fitted into hand piece 1. The medial segment 33 continues until it reaches stem 18 at the distal end of the hand piece.

Fore of the medial segment 33, the hand piece bore 30 makes three discrete step-ups or increases in inner diameter. The step-ups are designed to interact with a second collet and bayonet fitting 60 (discussed below) which secures sheath 3 to hand piece 1 and also adjusts the amount by which sheath 3 extends beyond and fore of hand piece 1. The second collet and bayonet fitting 60 has corresponding step-downs in diameter, producing a tiered or terraced effect.

The first step-up in inner diameter is at segment 34, which receives most proximal tier 69 of bayonet fitting 61. The second step-up is at segment 35, which receives the next tier 67 of the bayonet fitting. The third step-up is at 36, which receives the distal tier 65 of the bayonet fitting. In the wall surrounding segment 36 are ring grooves 39 (not shown in FIG. 2) formed to receive bayonet pins 66a and 66b.

Turning now to FIGS. 4a–4c for the details of the first collet arrangement 40, the tubular shaft 16 of endoscope 2 (not shown in FIGS. 4a–4c) is held within the hand piece 1 by the first collet 40 at the proximal end of the hand piece. The first collet 40 has four components: (i) a locking nut 41; (ii) a gasket (O-ring) 48; (iii) a compression fitting 50; and (iv) a seat or bushing 57. The locking nut 41 is threaded into the proximal segment 31. The nut 41 compresses compression fitting 50 against bushing 57, and thereby secures a snug grip on the tubular shaft 16 of the endoscope.

The distal end of locking nut 41 has a stem 42, to the outer surface of which male threading 43 has been set. By these threads the locking nut can be engaged into female threads formed on the inside of the proximal segment 31 of the hand piece bore. The outer diameter of stem 42 is smaller than the diameter of the proximal segment 31 and slightly larger than the outer diameter of the tubular shaft 16 of an endoscope. At the proximal end of locking nut 41 is a knurled hub 44. To secure the locking nut 41 into the hand piece 1, one rotates the hub 44 clockwise. The locking nut is made of 300 series stainless steel. It is given a passivated finish, with all burrs and sharp edges removed.

A bore extends through the locking nut 41 along its longitudinal axis. The bore has two segments: stem bore 45 and hub bore 46. The inner diameter of the stem bore 45 gradually decreases distal to proximal, so as to accommodate the increasing diameter of the compression fitting 50. The stem bore 45 also has a detent 47 to give a back stop to brace the compression fitting 50. The stem bore 45 communicates with the hub bore 46 which extends through the hub 44 along its longitudinal axis. The hub bore 46, however, has a larger diameter than the stem bore 45, and thus facilitates the placement and alignment of the tubular shaft 16 of the endoscope.

The gasket or O-ring 48 fits over the threaded portion 43 of the stem 42. As the stem 42 is cinched to the hand piece 1, the gasket 48 provides a seal so that the irrigants and aspirants do not leak.

The bushing 57 is a metal ring that seats at the distal end of the threading formed on the segment 30 of the hand piece bore. A slight decrease in the inner diameter of the segment 30 at the distal end of the threading 31 forms a step or detent segment 47 against which the bushing 57 abuts and is braced. A bore 58 is formed within the bushing 57 along its longitudinal axis. The diameter of the bore 58 is greatest at the proximal end of the fitting and then grows progressively smaller, until it takes its smallest dimension at the distal end. The bore 58 of the bushing 57 decreases so that it may accommodate the corresponding shape of the compression fitting 50. Like the locking nut 41, the bushing 57 is made of series 300 stainless steel and given a passivated finish with burrs and sharp edges removed.

The compression fitting 50 is preferably made of gray polyvinylchloride plastic. A cylindrical bore 51 runs through the fitting 50 along its longitudinal axis. The inner diameter of the bore 51 is uniform and slightly larger than the outer diameter of the tubular shaft 16 of the endoscope. At the distal end of the fitting, the outer diameter holds constant at a seating shank 52 for a length sufficient to allow the distal end to be inserted into the proximal end of the bushing 57 and seated therewith. From the proximal end of the seating shank 52, however, the outer diameter of the fitting 50 gradually increases to a central area 53 of the fitting, and then gradually decreases to the proximal end of the fitting, such that the outer diameters, 54a and 54b, at either end of the fitting 50 (and the distal end of seating shank 52) are the same, and such that the gradual increase and decrease of the outer diameter to and from the mid-lengths are symmetrical. A thin cut or slit 55 is made in the fitting 50, running parallel to the longitudinal axis of the fitting. Another seating shank, identical to the first seating shank 52, can be added to the proximal end of the fitting 50, thus allowing the user to insert either end of the fitting 50 into the bushing 57.

The compression fitting 50 is seated in the bore 30 of the hand piece, to lie between the bushing 57 and the locking nut 41. As the stem 42 of the locking nut 41 is threaded into the hand piece, it advances. As the inner diameter of the stem 42 advances, it reaches the gradually increasing outer diameter of the fitting 50 and then begins to compress the fitting 50. The fitting 50 is able to compress in response to the advance of stem 42 by virtue of the thin cut 55 made within the wall of the fitting 50. As the fitting compresses, the inner diameter, formed by the bore 51 therein, becomes smaller, and thereby secures a friction fit to hold the tubular shaft 16 of the endoscope seated therein.

It will be understood that other means besides the described collet assembly may be used to adaptably fit the hand piece to the endoscope. Among such means are a chucking mechanism at the proximal bore of the hand piece; leaf springs set in the proximal bore 17 of the hand piece; a cam and lever mechanism to cinch down on the endoscope; or different sizes of O-rings to grip the endoscope as well as provide a tight seal, to be cinched down by means of a standard size locking nut.

Referring to FIG. 4, details of the second collet and bayonet fitting arrangement 60 as illustrated. Fitted onto the sheath 3 are: (i) a bayonet fitting 61; (ii) a locking nut 72; and (iii) a compression fitting 78. Each of the three components has an internal bore with an inner diameter greater than the outer diameter of the sheath 3 and are thus able to slidably fit onto the sheath 3. At the proximal end of the sheath 3 is the bayonet fitting 61; at the distal end of the sheath is the locking nut 72. Between the bayonet fitting 61 and the locking nut 72 is the compression fitting 78.

The proximal end of the sheath 3 has a slight flare or flange 80, such that bayonet the fitting 61 cannot slide off the proximal end of the sheath. The sheath 3, though cylindrical when first manufactured, is slightly flattened from region 19 to the distal end, making the sheath slightly oblong. Such a shape better accommodates the entry and flow-through of tissue debris through the annular space 29. Also, once the bayonet fitting 61, the locking nut 72 and the compression fitting 78 have been set on the sheath 3, and the sheath is slightly flattened from region 19 forward, the locking pieces and fitting cannot slide off the distal end of the sheath, either. At the distal end of the sheath 3, a small hole 81 is made into the sheath wall. The hole 81 allows for a portion of the irrigant to cleanse tissue lateral to the sheath, as in sinus surgery the frontal sinus. The distal end of the sheath is given a small inward roll or lip 82 so as to divert a portion of the irrigant to flush the distal optics of the tubular shaft 16.

The bayonet fitting 61 has an inner cylindrical bore having diametral dimensions larger than the outer diameter of the tubular shaft 16 of the endoscope. The outer structure of the bayonet fitting 61 has four annuluses or step-downs that have progressively smaller diameters, providing a tiered or terraced arrangement.

Starting from the distal end of the bayonet fitting 61 is a hub 62, which is the first tier. Two turning spindles 63a and 63b are set in the rim of the hub 62. Because the hub is used to provide the torque to lock bayonet pins 66a and 66b in place, it has the greatest outer diameter of the four tiers and is knurled on its rim.

Abutting the hub 62 is a second tier 65 holding the two bayonet pins 66a and 66b. The bayonet pins 66a and 66b insert into corresponding ring grooves 39 formed in the wall of the bore segment 37. The bayonet arrangement serves to hold the sheath 3 in fixed longitudinal alignment, i.e. along the z-axis. The outer diameter of the second tier 65 is therefore similar to the inner diameter of the corresponding bore segment 37. The length of the second tier 65 is slightly smaller than the length of the segment 37; the difference in these lengths is slightly smaller than depth to which the grooves 39 move into the hand piece wall of segment 37. In this manner, as the bayonet pins 66a and 66b are inserted into the grooves and twisted to be seated therein, the proximal face of the second tier 65 is pulled toward the bayonet ledge 38 formed by the diametral difference between the segments 37 and 35. The bayonet arrangement thus also serves to form a secure, snug fit between the hand piece and the sheath.

Abutting the second tier 65 is third tier 67. The outer diameter of the third tier 67 is approximately equal to the inner diameter of a gasket or O-ring 68 seated on the ledge 36 formed by the diametral difference between the segments 37 and 35 of the hand piece bore. The length of the third tier 67 is slightly smaller than the length of segment 35 (less the length of the gasket 68), such that as the bayonet pins 66a and 66b are twisted and seated, the third tier 67 and the gasket 68 are pulled together to form a tight seal against leaking of the irrigant and aspirant.

Abutting the third tier 67 is a fourth tier 69, which is the last step-down. The outer diameter of the fourth tier 69 is similar to the inner diameter of the segment 34 of the hand piece bore. The fourth tier 69 and its corresponding fore segment 34 serve the purpose of holding the sheath in fixed radial x-y planar alignment. The length of the fourth tier 69, and the length of corresponding segment 34, are similar, and are relatively greater than the lengths of the third tier 67 and the second tier 65, and the corresponding segments 35 and 37, respectively. The lengths of the fourth tier 69 and segment 34 are greater so that a more secure x-y alignment may be attained.

Bayonet fitting 61 is made of series 300 stainless steel and given a passivated finish with burrs and sharp edges removed.

It is the length of the second tier 65 and the bayonet ledge 38 that are the primary and practical limits of the degree to which the bayonet fitting 61 is inserted into the hand piece. While the gasket ledge 36 provides a detent to the third tier 67, the length of the second stepped portion, the segment 35, is slightly greater than the length of the third tier 67 and therefore as a practical matter this detent does not control the depth of insertion. The gasket ledge 36, formed by the diametral difference between the segments 35 and 37, serves rather as a seat for the gasket 68.

The proximal end of the sheath may be positioned and secured so that it aligns flush with the end of the fourth tier 69. The proximal end of the sheath may also be extended and secured beyond the end of fourth tier 69. A flange 80, while flared enough to prevent the bayonet fitting 61 from slipping off, is not so great as to prevent the sheath from being inserted to abut the bushing 57 of the first collet arrangement 40. As a practical matter, however, the sheath 3 is extended into the hand piece only so far as necessary so that the distal end of the sheath 3 aligns flush or near flush with the distal end of the tubular shaft 16 of the endoscope.

If the sheath 3 is inserted into the mid-portion of the hand piece, it will interfere with the flow of irrigant and aspirant at ports 24a and 24b. It is possible to limit the degree to which the sheath may be inserted into the hand piece by crimping and flattening a portion of the sheath at a sheath region 19, which is fore of the second collet and bayonet fitting arrangement 60. The portion of the sheath that is thus made oblong will not slip through bayonet fitting 61.

The first and second tiers, 62 and 65, of the bayonet fitting also cooperate with the compression fitting 78 and locking nut 72 to hold the sheath at a selected length or extension from the hand piece. A bore runs through the bayonet fitting 61, having a proximal bore portion 70 and a distal bore portion 71. Whereas the proximal bore 70 runs through the fourth tier 69, the third tier 67 and the proximal portion of the second tier 65 and approximates the outer diameter of the sheath 3, the distal bore 71 runs through the distal portion of the second tier 65 and through the first tier 62 and has a larger diameter. The walls of distal bore 71 are given female threading 64, so as to engage male threading 77 on the locking nut 72.

The locking nut 72 has a stem portion 73 and a hub portion 74. The stem portion 73 is at the proximal end of the locking nut. It is generally cylindrical and has an axial bore 75. The stem 73 has male threading 77 formed on its outer surface; by these threads the locking nut can be threaded into female threads 64 formed on the inside of the distal bore 71 in the first and second tiers 62 and 65 of the bayonet fitting 61. The outer diameter of the stem portion 73 and the inner diameter of the distal bore 71 are therefore approximately equal.

At the proximal end of locking nut 72 is a knurled hub 74. To thread the locking nut 72 into the bayonet fitting 61, one rotates the hub 74 clockwise. The hub 74 also has an axial bore 76, sharing the same longitudinal axis as the stem bore 75.

The diameter of the hub bore 76 in the hub 74 approximates the outer diameter of the sheath 3. The diameter of the bore 75 in the stem portion 73 is greater, for it must coact with the compression fitting 78 and the bayonet fitting 61.

Like the first locking nut 41, the second locking nut 72 is made of series 300 stainless steel and given a passivated finish with burrs and sharp edges removed.

Unlike the compression fitting 50 of the first collet 40, the compression fitting 78 of the second outlet 60 can be made of metal and frustoconical. The smaller face of the frustum fits into the stem portion 73; the larger face fits into the distal bore 71 of bayonet fitting 61. The compression fitting 78 has a coaxial bore with a diameter approximating the outer diameter of sheath 3. Like the first compression fitting 50, it too has a thin cut or sliver 79 taken from the wall and parallel to the longitudinal axis. As the locking nut 72 is threaded into the distal bore 71 of the bayonet fitting 61, the compression fitting 78 is compressed, and as its inner diameter becomes smaller, it forms a snug fit on the sheath 3. In this manner, it is possible to select the length to which the sheath 3 is to be extended from the hand piece and then to secure that extension by means of the second collet 60.

The compression fitting 78 is made of series 300 stainless steel and given a passivated finish with burrs and sharp edges removed.

Naturally, it is possible to use a bayonet fitting 61 of four tiers that is integrated onto the sheath 3. Such a fitting is available from Circon as part number 006908-901. But such an embodiment does not allow for adjustment in the length to which the sheath 3 may be extended. Such an embodiment, nevertheless, allows for scopes of different diameters (of the same extension length) to be used with a single form of hand piece as in the present invention.

As noted above, the sheath 3 is secured to the distal end the hand piece by means of the bayonet fitting 61 which cooperates with the ring grooves 39 in the distal end of the hand piece bore and which is slidably fitted onto the sheath 3. A second collet, comprised in part of the compression fitting 78 and the locking nut 72, is also fitted onto the sheath, allows for adjustment in the length to which the sheath 3 is extended from the hand piece.

In FIG. 7a there is illustrated how the sheath may be fashioned at its distal end to provide mechanical action on the tissue being treated. The distal end of sheath 3 may be shaped so as to serve like mechanical, hand-held instruments. A portion 90 of the distal rim of the sheath may be pointed and sharpened to enable tissue cutting, like a scalpel. Alternately, FIG. 7b illustrates a portion 91 of the distal rim may be bluntly tapered and rounded to enable blunt dissection, like a surgical spatula.

In FIG. 8 is illustrated how electrosurgical capability may be imparted to the sheath 3. Electrical cables 100a and 100b connect to an electrosurgical generator (not shown) and lead into a hub 101 that slips onto the sheath 3, to abut the sheath locking nut 61. Electrical conductors 102a and 102b are connected within hub 101 to electrical cables 100a and 100b. The conductors 102a and 102b lead from the hub 101, either embedded into the sheath 3 or overlaid upon the sheath, to the distal end of the sheath. Each conductor may terminate in a prominence 103a and 103b near the distal end of the sheath, such that a bipolar electrical circuit is closed when tissue is held within and between the prominences. Alternately, the conductors 102a and 102b terminate near the distal end of the sheath and may be joined by a conductive bar having relatively greater resistance, such that conductive bar provides ohmic heating. Whether conductors 102a and 102b are within or upon the sheath, means are provided to insulate the conductors from leaking from the circuit and to hold the conductors stable. The powers used will necessarily be low, so as not to damage the distal optics of the endoscope.

In FIG. 9 is illustrated how the sheath 3 may be supplemented with laser capability. An optical fiber 110, protected by a loose coaxial jacket or sheath 111, connects to a laser source (not shown) and leads into a hub 112 that slips onto sheath 3, to abut the sheath locking nut 61. The optical fiber 110 leads from the hub 112, and is overlaid and secured to the surface of the sheath 3. The optical fiber 110 terminates near the distal end of the sheath. A small fiber hub 113 fitted to the coaxial fiber jacket 111 at the distal end of the fiber allows various laser probes to be threadedly attached to the fiber. Among such probes are ones that may be used for forward or lateral coagulation or vaporization of tissue, either in contact with the tissue being treated or not. A rounded, side-firing contact probe 114 is shown mounted to connection hub 113. Such probes may be cooled by a coolant that flows in an annular space between the optical fiber 110 and the coaxial fiber jacket 111.

A nozzle instead of a probe 114, may be mounted to the small hub 113 at the distal end of the fiber, and the pressure forcing fluid through the annular space between the optical fiber 110 and the coaxial jacket 111 may be increased. The increase in pressure and the constricted outflow from the nozzle enables a directed flow of fluid to the tissue site. It is possible to heat such fluid, as the irrigant may be heated, to achieve specific therapeutic effects.

In FIG. 10 is illustrated how the sheath 3 may be supplemented with enhanced viewing elements. Enhanced visualization of the surgical site may be achieved by image-guided surgery. Such capability may be added by way of a sensor 120 at the distal end of sheath 3, that can provide visibility of the location of the underlying sheath 3. The sensor 120 has leads 121a and 121b that enter a hub 122, and from the hub attached to cables 123a and 124b which connect to a sensing monitor 124. The leads 121a and 121b may be protected from surgical rigors by the hub 122 and surface securing means that hold the optical fiber or electrosurgical conductors on the surface of the sheath. Exemplary sensing devices are manufactured by Biosense, Inc. (Tel Aviv, Israel) and Visualization Technology, Inc. (Woburn, Mass.).

The invention may be constructed of materials which are compatible with magnetic resonance imaging ("MRI"), which is used to guide a surgeon in certain surgical procedures, especially in neurosurgery. In order to have minimal distortion or interference on the magnetic field, the metal components of the invention should be made of a non-interfering substance, as for example titanium or ceramic.

The hand piece 1 can be inexpensively made of plastic, and therefore rendered a disposable, to be discarded after a single surgical procedure. Using plastic instead of metal also significantly reduces the weight of the hand piece. The sheath 3, on the other hand, being generally cylindrical with a smooth uniform inner bore, lends itself to ready cleaning and resterilization and therefore can be inexpensively made of a surgical grade metal and re-used.

The preferred embodiment of the present invention is used in the following manner. The device will have been packaged in sterile condition. It will be opened in the sterile field and attached to the endoscope before surgery.

After an endoscope 2 has been inserted into the hand piece 1, the first collet 40 is adjusted to secure a snug fit on the tubular shaft 16 of the endoscope. The hub 44 will be turned clockwise. Yet the hub 44 will not be turned so far as to prevent small rotation of the tubular shaft 16 of the endoscope.

Where the hand piece 1 has a second collet arrangement 60, the length by which the sheath 3 extends from the hand piece 1 will be adjusted, preferably to end flush or near flush with the distal end of the tubular shaft 16 of the endoscope. The locking nut 72 of the collet will be turned clockwise. Nevertheless, the locking nut 72 will not be turned so far as to prevent small rotation of the sheath 3.

If the sheath has been fashioned at the distal end to provide mechanical action, then the user will retract the endoscope or alternately extend the sheath (which does not require adjustment of the first collet), such that the sheath terminates fore of the endoscope. The mechanical working area of the sheath now being exposed, the user may exert mechanical force upon tissue being treated.

If the sheath has been given electrosurgical coagulating capability, then the user will retract the endoscope or alternately extend the sheath (which does not require adjustment of the first collet), such that the sheath terminates fore of the endoscope. This is done in part to protect the tubular shaft from the electrical current and to minimize interference between the two. The electrosurgical capability may now be implemented upon the tissue being treated.

The tissue is positioned to lie between the contact points. Enough electrical power is provided to cause the current to flow from one point, through the tissue, to the other point. No arcing is necessary or desirable. The power should be kept as low as possible, so as to prevent charring of the tissue. As soon as the tissue begins to dry out and blanch, it is generally desirable to cease coagulation of the tissue between the points. If coagulation is continued, the coagulum becomes hard and tends to cling to the points, thus obstructing the flow of current. Low powers should be used so as not to damage the optics at the distal end of the tubular shaft, and frequent visual checks of the progress should be made.

Where the sheath has been imparted laser capability, then the user may, but need not, retract the endoscope or extend the sheath. If a probe is connected to the distal end of the fiber, then coolant should be provided to the junction between the fiber and the probe. If a probe is selected for lateral tissue effect, then the scope will preferably have an angled field of view. Care should be taken to use the laser in small doses, and frequent visual checks of the progress should be made.

A nozzle, instead of a probe, may be mounted to the small hub 113 at the distal end of the fiber, and the pressure forcing coolant through the space between the optical fiber and the jacket may be increased. The increase in pressure and the constriction in the outflow by the nozzle enable a directed flow of fluid to the tissue site. It is possible to heat such fluid, as the irrigant may be heated, to achieve specific therapeutic effects.

The irrigant may be used to deliver a drug to the tissue being treated, or if finer control is desired, a liquid impregnated with the drug may be delivered to the tissue through the coaxial sheath of the optical fiber.

In certain procedures, irrigant liberally applied to the surgical site may show how access may be gained to tissue otherwise obscured. Liberal irrigation can gently part soft tissue that lies over other tissue that is to be treated. Irrigation can also be used to point the way to tissue otherwise hard to discern. For example, a trail of bubbles from the irrigant may emerge from the sphenoid ostium and thus guide the way to the sphenoid sinus.

The present invention may be embodied in other specific forms without departing from the spirit or essential attributes thereof and, accordingly, reference should be made to the appended claims, rather than to the foregoing specification, as indicating the scope of the invention.

What is claimed is:

1. A surgical hand piece for providing irrigation and aspiration to a surgical field for use in conjunction with a variety of endoscopes having shafts of different outside diameters, the hand piece comprising:

a through bore for receiving an endoscope;

means for securing endoscope shafts of varying outside diameters to the hand piece.

2. A surgical hand piece as recited in claim 1, wherein the means for securing the endoscope shafts to the hand piece comprises:

a compression fitting having a proximal end and a distal end, an outer diameter that increases from the proximal end to a center portion and then decreases from the center portion to the distal end, and a central longitudinal bore for receiving an endoscope shaft; and a locking nut having a longitudinal bore of a diameter greater than the outer diameter of the compression fitting at the proximal end of the fitting, the locking nut receiving the compression fitting and the through bore receiving the locking nut.

3. A surgical hand piece as recited in claim 2, wherein the compression fitting includes a longitudinal slit along the entire length of the fitting.

4. A surgical hand piece for providing irrigation and aspiration to a surgical field for use in conjunction with a variety of endoscopes, the hand piece comprising:

a through bore for receiving an endoscope;

means for securing a sheath to the hand piece at a distal opening of the bore.

5. A surgical hand piece as recited in claim 4, wherein the means for securing the sheath to the hand piece comprises:

an attachment fitting received by a distal opening of the hand piece bore, having a proximal stem including a bore of a diameter greater than an outer diameter of the sheath;

a compression fitting having an inner diameter greater than the outer diameter of the sheath and an outer diameter that increases from a distal end to a proximal end; and a locking nut having an inner diameter increase from a distal end to a proximal end and receives the compression fitting and is received by the attachment fitting.

6. A surgical hand piece as recited in claim 5, wherein the compression fitting includes a longitudinal slit for the entire length of the fitting.

7. The hand piece as recited in claim 4, further comprising means to vary the length by which said sheath extends from said hand piece.

8. The hand piece as recited in claim 4, further comprising means formed on the distal end of said sheath for providing mechanical force upon tissue being examined or treated surgically.

9. The hand piece as recited in claim 4, further comprising means to coagulate tissue being examined or treated surgically.

10. The hand piece as recited in claim 9, wherein the means to coagulate tissue is electric energy.

11. The hand piece as recited in claim 9, wherein the means to coagulate tissue is laser energy.

12. The hand piece as recited in claim 9, wherein the means to coagulate tissue is warmed liquid.

13. The hand piece as recited in claim 4, further comprising means for delivering a drug to tissue being examined.

14. The hand piece as recited in claim 4, further comprising means for providing an irrigant under pressure to a surgical site.

15. The hand piece as recited in claim 4, further comprising means for providing real time sensing capability.

16. The hand piece as recited in claim 4, wherein the hand piece and associated elements are constructed of materials that are compatible with magnetic resonance imaging.

17. A method of adjustably attaching a sheath and endoscope to a hand piece which provides aspiration and/or irrigation, the hand piece comprising means, used in conjunction with the sheath, for coupling said endoscope to said hand piece, means for coupling said sheath to the hand piece, the hand piece for use in conjunction with a variety of endoscopes, said method comprising the following steps:

inserting a selected one of said variety of endoscopes into said hand piece;

adjusting said endoscope coupling means to hold said endoscope securely to the hand piece yet permit rotation of said endoscope;

inserting the sheath into said hand piece;

adjusting said sheath coupling means to hold said sheath securely to the hand piece yet permit rotation of said sheath.

18. The method of claim 17, further including the step of:

adjusting said sheath coupling means to vary the length by which said sheath extends from said hand piece.

19. The method of claim 18, further including the steps of:

adjusting said endoscope coupling means and said endoscope such that said sheath extends further from said hand piece than said endoscope enabling mechanical force to be exerted upon tissue being treated by said sheath.

20. The method of claim 18, further including the steps of:

adjusting said endoscope coupling means and said endoscope such that said sheath extends further from said hand piece than said endoscope enabling tissue being treated to be coagulated by coagulating means formed on a distal portion of the sheath.

* * * * *